US00PP11457P

United States Patent [19]

van der Knaap

[11] Patent Number: Plant 11,457

[45] Date of Patent: Jul. 18, 2000

[54] SPATHIPHYLLUM PLANT NAMED 'SPAREGO'

[75] Inventor: Adrianus Leonardus Joseph van der Knaap, Naaldwijk, Netherlands

[73] Assignee: KP Holland Selection, Naaldwijk, Netherlands

[21] Appl. No.: 09/177,289

[22] Filed: Oct. 22, 1998

[51] Int. Cl.[7] ..... A01H 5/00

[52] U.S. Cl. ..... Plt./364

[58] Field of Search ..... Plt./364

[56] References Cited

U.S. PATENT DOCUMENTS

P.P. 9,677 10/1996 Osiecki ..... Plt./364

P.P. 10,146 12/1997 Caldwell ..... Plt./364

P.P. 10,615 9/1998 Osiecki ..... Plt./364

P.P. 10,895 5/1999 van Es ..... Plt./364

*Primary Examiner*—Howard J. Locker

*Assistant Examiner*—Kent L. Bell

*Attorney, Agent, or Firm*—C. A. Whealy

[57] ABSTRACT

A distinct cultivar of Spathiphyllum plant named 'Sparego', characterized by its upright, outwardly arching and very freely clumping growth habit; large, glossy, dark green leaves that are oblong/elliptic in shape; numerous inflorescences that are positioned upright and above the foliage on strong and erect scapes; large white spathes; year-round continuous flowering; and good post-production longevity.

2 Drawing Sheets

BACKGROUND OF THE INVENTION

The present invention relates to a new and distinct cultivar of Spathiphyllum plant, botanically known as Spathiphyllum spp., and hereinafter referred to by the cultivar name 'Sparego'.

The new Spathiphyllum is a product of a planned breeding program conducted by the Inventor in Naaldwijk, The Netherlands. The objective of the program is to create new Spathiphyllum cultivars that have large, glossy, dark green leaves, large white spathes, continuous yearround flowering, and good post-production longevity.

The new Spathiphyllum originated from a cross by the Inventor in January, 1993 of the Inventor's proprietary Spathiphyllum spp. selection code number 701 as the female, or seed, parent with the Inventor's proprietary Spathiphyllum spp. selection code number 708 as the male, or pollen, parent. The cultivar 'Sparego' was discovered and selected by the Inventor as a plant within the progeny of the stated cross in a controlled environment in Naaldwijk, The Netherlands in November, 1994.

Asexual propagation of the new cultivar by tissue culture in Roelofarendsveen, The Netherlands, has shown that the unique features of this new Spathiphyllum plant are stable and reproduced true to type in successive generations of asexual propagation.

BRIEF SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Sparego'. These characteristics in combination distinguish 'Sparego' as a new and distinct cultivar:

1. Upright, outwardly arching and very freely clumping growth habit.

2. Large, glossy, dark green leaves that are oblong/elliptic in shape.

3. Numerous inflorescences that are positioned upright and above the foliage on strong and erect scapes.

4. Large white spathes.

5. Year-round continuous flowering.

6. Good post-production longevity.

The new Spathiphyllum can be compared to the female parent, the Inventor's proprietary selection code number 701. In side-by-side comparisons conducted by the Inventor in Naaldwijk, The Netherlands, plants of the new Spathiphyllum have darker green and glossier leaves than plants of the selection code number 701.

The new Spathiphyllum can be compared to the male parent, the Inventor's proprietary selection code number 708. In side-by-side comparisons conducted by the Inventor in Naaldwijk, The Netherlands, plants of the new Spathiphyllum have larger glossier leaves and larger spathes than plants of the selection code number 708.

The new Spathiphyllum can be compared to the Spathiphyllum cultivar 'Lynise' disclosed in U.S. Plant Pat. No. 6,145. In side-by-side comparisons conducted by the Inventor in Naaldwijk, The Netherlands, plants of the new Spathiphyllum differ from plants of the cultivar 'Lynise' in the following characteristics:

1. Plants of the new Spathiphyllum have larger and glossier leaves than plants of the cultivar 'Lynise'.

2. Plants of the new Spathiphyllum have larger spathes and spadices than plants of the cultivar 'Lynise'.

3. Young spathes of plants of the new Spathiphyllum are white whereas young spathes of plants of the cultivar 'Lynise' are greenish white.

BRIEF DESCRIPTION OF THE PHOTOGRAPHS

The accompanying colored photographs illustrate the overall appearance of the new Spathiphyllum, showing the colors as true as it is reasonably possible to obtain in colored reproductions of this type.

The photograph on the first sheet comprises a side perspective view of a typical potted plant of the cultivar 'Sparego'.

The photograph on the second sheet comprises a close-up view of a typical spathe and spadix of the cultivar 'Sparego'. Leaf, spathe and spadix colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in 28-cm containers in Naaldwijk, The Netherlands, in a glass greenhouse with an average day temperature of 21.5° C. and an average night temperature of 21.5° C.

Botanical classification: Spathiphyllum spp. cultivar 'Sparego'.

Parentage:

*Female parent*.—Inventor's proprietary Spathiphyllum spp. selection code number 701.

*Male parent*.—Inventor's proprietary Spathiphyllum spp. selection code number 708.

Propagation:

*Method*.—Typically by tissue culture.

*Time to initiate roots*.—About 11 to 14 days at 21° C.

*Rooting habit*.—Numerous fleshy roots.

Plant description:

*Plant shape*.—Upright, inverted triangle, symmetrical.

*Growth habit*.—Erect when young, becoming outwardly arching as leaves develop. Freely clumping, bushy and dense. Appropriate for 17-cm and larger containers.

*Plant height*.—About 95 cm from soil level to apex of spathes.

*Plant vigor*.—High.

*Growth rate*.—Moderate.

*Crop time*.—About 45 weeks are usually required from planting of young plants to finished plants in 17-cm containers.

*Foliage descriptions*.—Quantity: Usually about 55 leaves per clump. Length: About 35 cm. Width: About 15 cm. Shape: Oblong/elliptic. Apex: Apiculate, cirrhous. Base: Obtuse. Margin: Entire. Texture: Smooth, glabrous, glossy, slightly undulate. Color: Young leaves, upper surface: Darker than 143A to 144A. Young leaves, lower surface: Close to 138B to 138C. Mature leaves, upper surface: Close to 139A; venation, 139A. Mature leaves, lower surface: Close to 139C; venation, 144A. Petiole: Length: About 45 cm. Color: Close to 137B.

Inflorescence description:

*Inflorescence arrangement*.—Spathe with spadix held above the foliage. Flowering structures arise from leaf axils. Freely flowering; continuous flowering year-round; typically three to ten inflorescences per plant.

*Inflorescence longevity*.—Inflorescences last about three weeks under interior conditions; persistent; fragrant.

*Flowers*.—Quantity of flowers per spadix: Numerous, about 150 to 200 flowers. Shape: Slightly conical. Diameter: About 2.5 mm.

*Spathe*.—Length: About 21.5 cm. Width: About 13.5 cm. Height above foliage: About 25 cm. Shape: Lanceolate to elliptic. Apex: Apiculate, cirrhous, undulating. Base: Cuneate. Margin: Entire. Aspect: Upright, erect. Texture: Glabrous, satiny, slight blistering. Color: When opening: White. Front surface: 155D; venation, 155A. Back surface: 155D, venation, 144A and 145B to 145C. After senescence: 145C to 145D.

*Spadix*.—Length: About 9.5 cm. Diameter: About 1.75 cm. Shape: Columnar. Cross section: Rounded. Longitudinal axis: Straight, erect. Color: 158A.

*Scape*.—Length: About 70 cm. Aspect: Strong and erect. Color: 137A to 139A.

*Reproductive organs*.—Androecium: Pollen color: Creamy white, 159B. Gynoecium: Stigma shape: Rounded.

Disease resistance:

Plants of the new Spathiphyllum have not been shown to be resistant to diseases common to Spathiphyllum.

Seed development:

Seed development on plants of the new spathiphyllum has not been observed.

It is claimed:

1. A new and distinct cultivar of Spathiphyllum plant named 'Sparego', as illustrated and described.

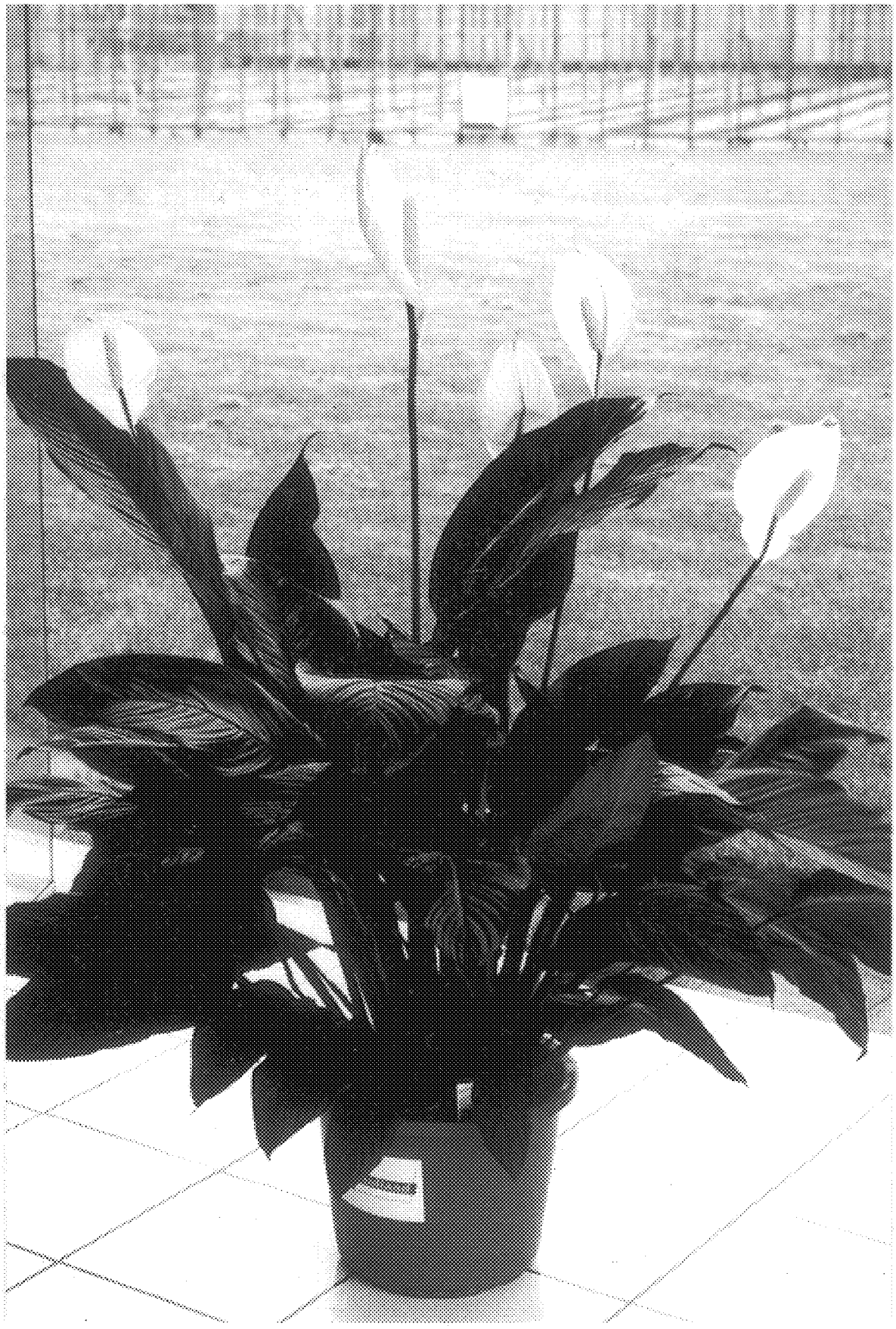

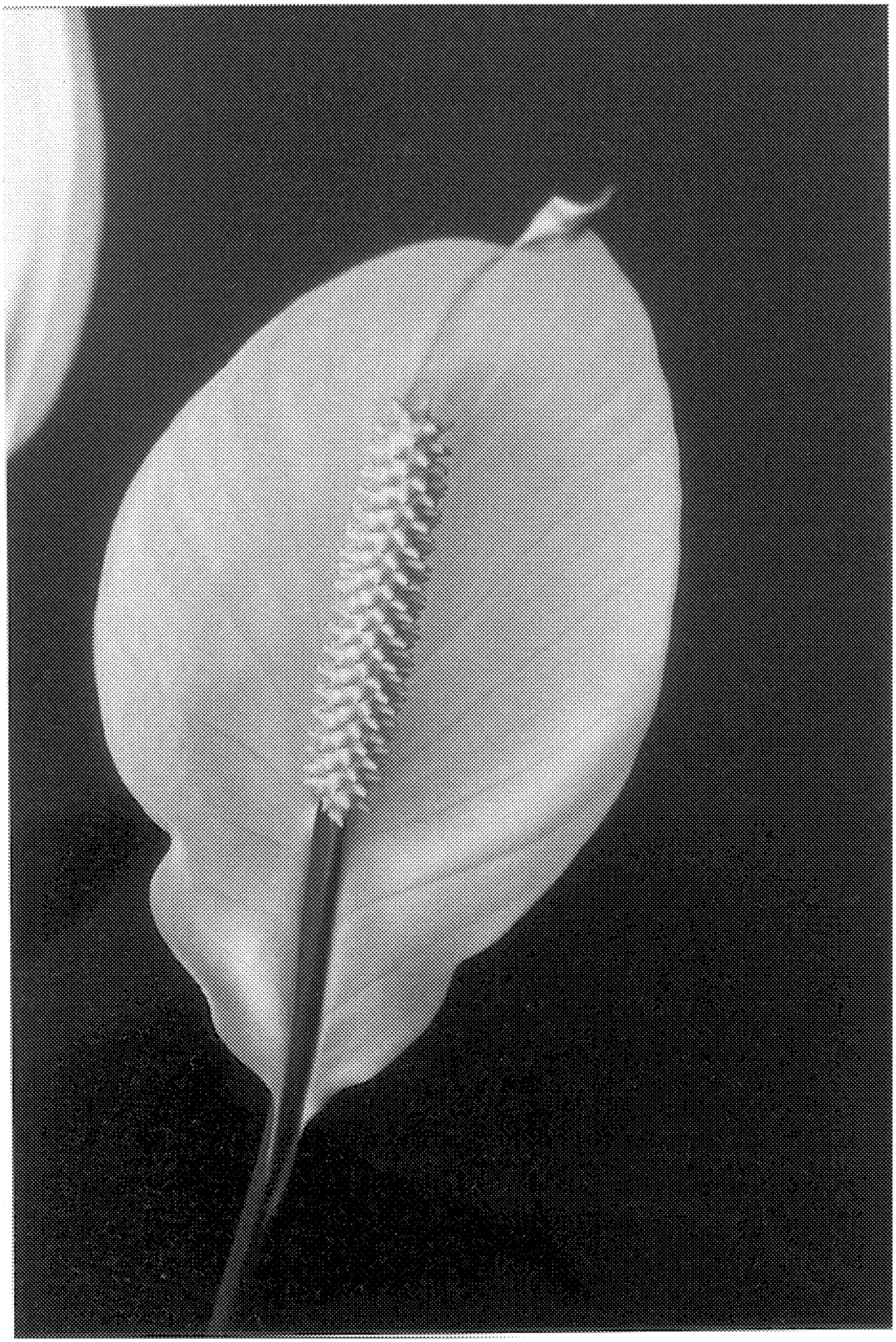

* * * * *